US007004950B1

(12) United States Patent
Collins et al.

(10) Patent No.: US 7,004,950 B1
(45) Date of Patent: Feb. 28, 2006

(54) TISSUE ALIGNING SURGICAL STAPLER AND METHOD OF USE

(76) Inventors: James R. Collins, 5817 Centralcrest, Houston, TX (US) 77092; Jock R. Collins, 5817 Centralcest, Houston, TX (US) 77092; Conard E. Kaiser, 5817 Centralcrest, Houston, TX (US) 77092

(*) Notice: Subject to any disclaimer, the term of this patent is extended or adjusted under 35 U.S.C. 154(b) by 477 days.

(21) Appl. No.: 10/177,936

(22) Filed: Jun. 21, 2002

(51) Int. Cl.
*A61B 17/04* (2006.01)

(52) U.S. Cl. .................... 606/142; 227/175.1
(58) Field of Classification Search ............. 606/219, 606/220, 75, 142, 143; 227/175.1, 179, 181.1, 227/19

See application file for complete search history.

(56) References Cited

U.S. PATENT DOCUMENTS

| 4,179,057 A | 12/1979 | Becht et al. |
| 4,485,953 A * | 12/1984 | Rothfuss ............. 227/19 |
| 4,506,669 A | 3/1985 | Blake, III |
| 4,582,237 A | 4/1986 | Storace et al. |
| 5,038,991 A | 8/1991 | Thornton |
| 5,423,856 A | 6/1995 | Green |
| 5,439,468 A * | 8/1995 | Schulze et al. ............. 606/143 |
| 5,893,855 A | 4/1999 | Jacobs |
| 5,937,951 A | 8/1999 | Izuchukwu et al. |

* cited by examiner

*Primary Examiner*—Julian W. Woo
(74) *Attorney, Agent, or Firm*—Kenneth A. Roddy

(57) ABSTRACT

A surgical stapler having a tissue spacer at its forward end. The spacer is inserted between lateral sides of a wound to be closed and holds the tissue on lateral sides of the wound apart while the tines of a staple are driven into the tissue margins and bent around the staple bending surface of the staple anvil to draw the tissue captured between the tines toward each other. The tissue spacer has a width greater than the width of the staple bending surface of the anvil and less than the distance between the tines of the staple in an unbent condition such that when inserted between lateral sides of the wound it will space the facing tissue margins of the wound apart a distance sufficient to provide a metered amount of tissue lateral sides of the wound that will be captured between the tines and drawn together as the tines are bent toward each other to close the wound without crushing or overlapping of the captured tissue.

19 Claims, 5 Drawing Sheets

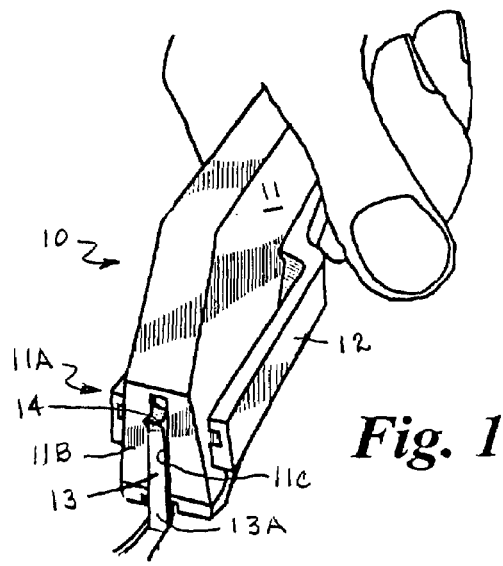
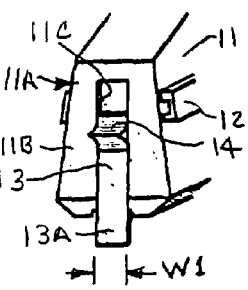
Fig. 1   Fig. 3A   Fig. 3B
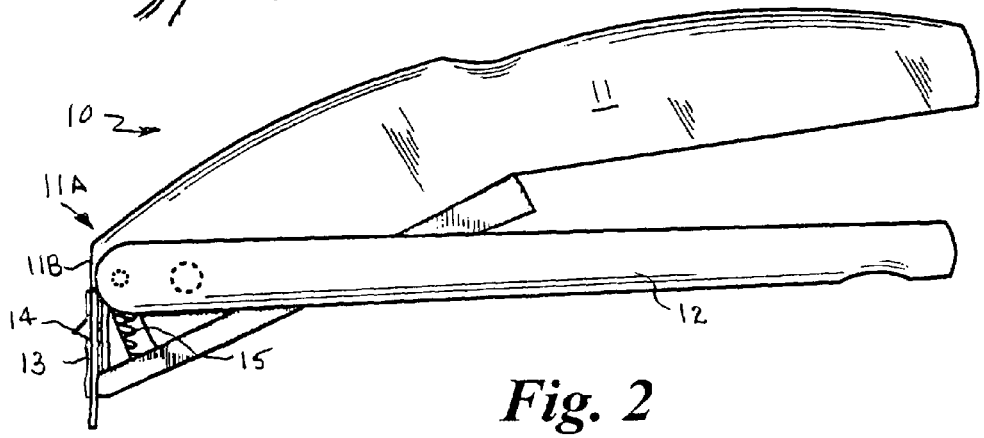
Fig. 2
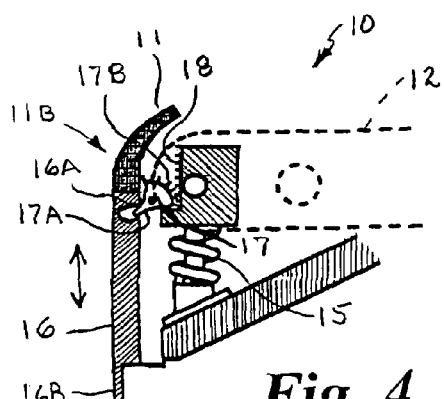
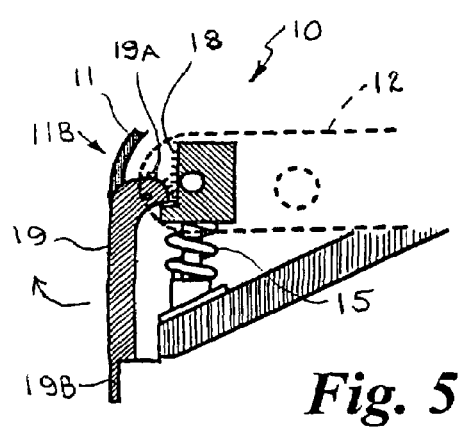
Fig. 4   Fig. 5

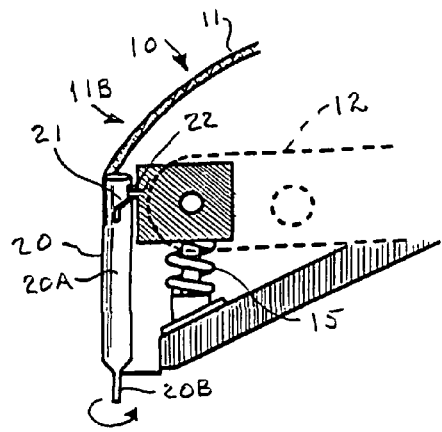 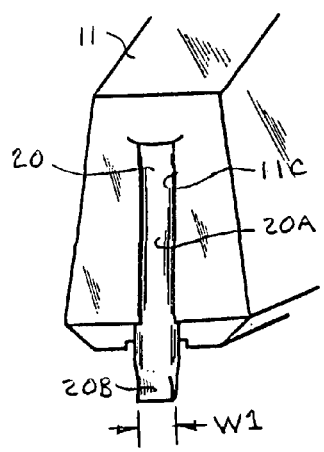 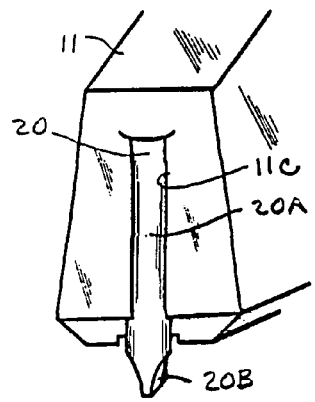
Fig. 7   Fig. 8A   Fig. 8B
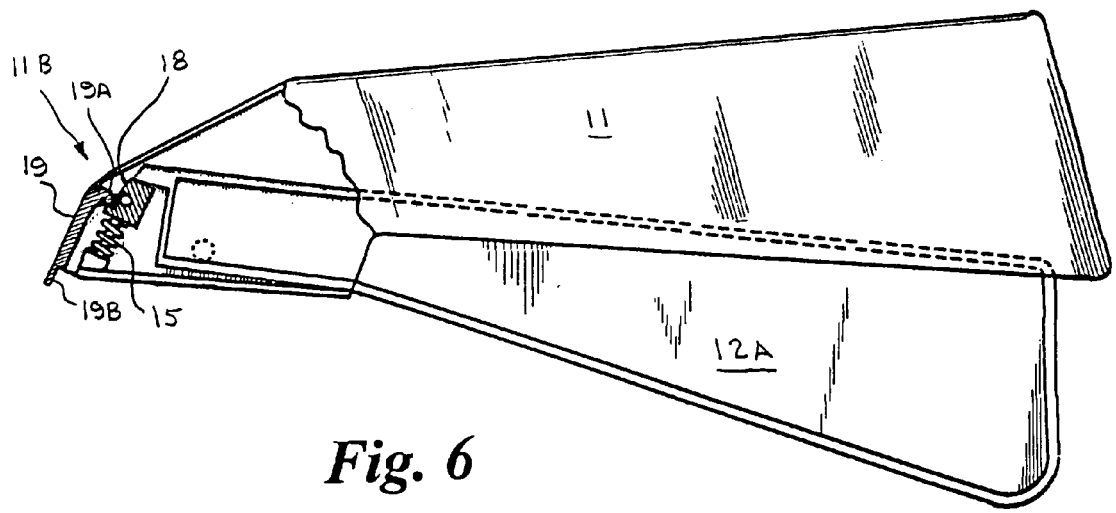
Fig. 6

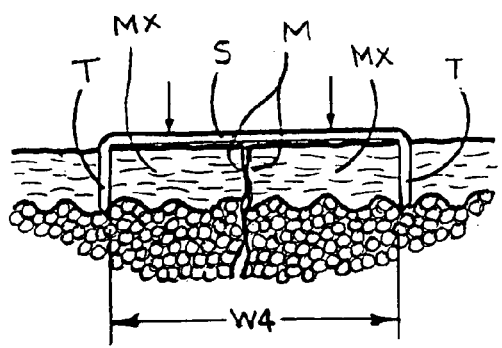
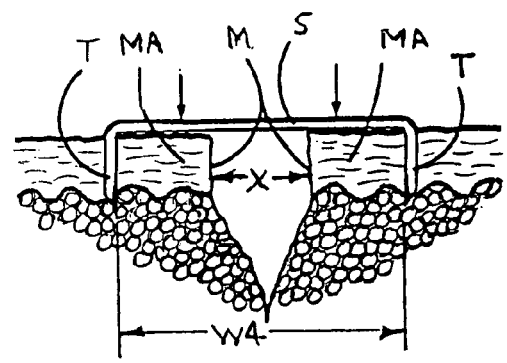
15A (Prior Art)
Fig. 14A
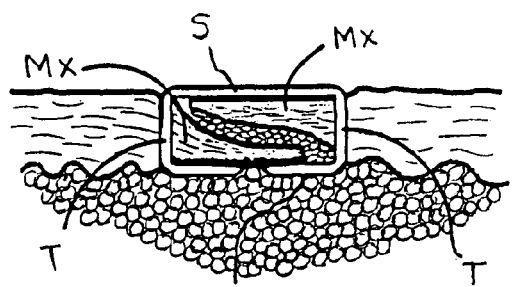
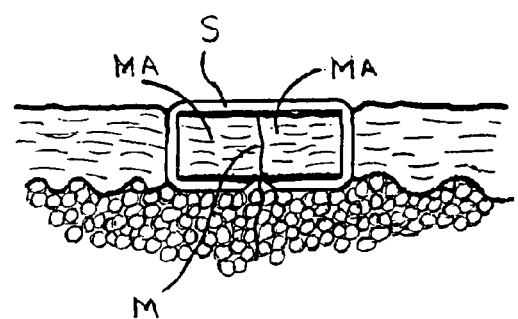
Fig. 15B (Prior Art)
Fig. 14B

TISSUE ALIGNING SURGICAL STAPLER AND METHOD OF USE

BACKGROUND OF THE INVENTION

1. Field of the Invention

The present invention relates to surgical staplers. More particularly, it relates to a surgical stapler having a tissue spacer that aligns, spaces and supports the tissue margins of a wound during a stapling procedure to avoiding overriding or crushing of tissues by the surgical staple upon closure.

2. Prior Art

Surgical staplers, also known as skin staplers, are surgical stapling instruments for implanting and forming surgical staples in the skin or fascia of a patient to close a wound or incision. The typical surgical stapler comprises an elongated body having a forward portion and a rearward portion serving as a handle portion. The forward portion of the instrument body houses a staple pusher or driver attached to a staple driver actuator and a return spring for the staple driver actuator. A surgical staple magazine assembly is affixed to the lower edges of the instrument body forward portion. An anvil plate, supporting a row of surgical staples, is located within the magazine assembly. The anvil plate terminates at its forward end in a coextensive anvil surface. The magazine assembly contains a feeder assembly to constantly urge the row of staples toward the anvil surface to locate the forwardmost staple of the row thereon to be implanted and formed thereabout by the driver and to disengage a formed staple therefrom. The magazine assembly also provides a channel for the lower end of the staple driver and a staple retaining surface to minimize bending of the staple crown during the staple forming operation. The staple driver is shiftable between a retracted position and a staple forming position by means of a trigger pivotally mounted to the instrument body forward portion and operatively connected to the staple driver actuator.

In these devices, the staple pusher or driver having an end with an inverted generally U-shaped recess advances a surgical staple, which is preformed in a broad-based, square-cornered U shape, downwardly toward the anvil plate. The base of the inverted U-shaped recess in the staple pusher or driver is broader or wider than the anvil plate, but not as broad or wide as the base of the U-shaped staple. When the staple reaches the anvil, the staple pusher or driver causes the staple to bend around the anvil into a closed, square-cornered C shape (known as forming the staple). As this is taking place, the ends or tines of the staple enter the tissue on the respective opposite sides of the incision or wound and draw the tissue together. When the staple has been fully formed, the staple pusher or driver is retracted and the stapler is removed. The staple remains in the tissue to hold it together during healing.

There are several patents that disclose surgical staplers or skin staplers with various features and a wide variety of feeding mechanisms to deliver each staple to the delivery point where the staple is deformed during implantation into the skin and/or tissue. See, for example: U.S. Pat. Nos. 4,179,057; 4,582,237; 5,038,991; and 5,937,951.

In addition to the surgical staplers and skin staplers identified above, there are other known skin approximator apparatus and combination surgical stapler and skin approximators for surgically stapling wounds.

U.S. Pat. No. 4,506,669 to Blake discloses a skin approximator consisting of a hinged device having two opposite disposed arms, each with a pair of barbs for engaging the skin on the opposite sides of the wound. Once engaged, the tissues are drawn together through a hinged motion of the arm thus allowing closure of the wound with a surgical staple placed in the conventional manner.

U.S. Pat. No. 5,423,856 to Green discloses an apparatus and method for surgical stapling comprising of a pair of side pointed jaws for engaging the tissues. The jaws are movable towards and away from each other. Once the tissues are approximated, the tissues are closed with a folding staple in the conventional manner.

U.S. Pat. No. 5,893,855 to Jacobs discloses an apparatus and method for the surgical stapling of body tissues. The invention consists of a surgical apparatus having a retractable approximation device that enables the operator to temporarily close the wound while positioning the staple injection port over the closed wound. Activation of the stapler stabs the staple tines into the tissues adjacent to the closed wound and then closes the staple within the tissues. An alternate embodiment provides for the use of asymmetrical staples that allows the longer staple leg to be stabbed into the tissues and thus used as an approximator before inserting the shorter leg of the staple. The staple is then bent in the conventional manner to close the wound.

The above-described patents are directed toward the closure of a wound with staplers and cumbersome combination approximation devices for the approximation of the wound edges prior to the placement of the surgical staples.

Currently, the conventional commercially available and most widely used staplers do not utilize cumbersome approximation devices but rather rely on the skill of the surgeon to approximate the margins of the wound.

In the current method of surgical stapling using conventional staplers, the surgeon approximates the wound margins, the stapler is centered over the wound, and the stapler is activated. The staple tines are inserted into the tissues and the staple is then bent closed. The activation of the handle or trigger on the stapler either retracts a central movable anvil between the sides of the inverted U-shaped recess in the staple pusher or driver, or the inverted generally U-shaped recess is lowered toward the anvil plate causing the staple to bend around the anvil into a closed, square-cornered C shape.

In either case the amount of tissue enclosed between the pointed ends of the staples as they are placed in the tissues is dependent on the skill and experience of the surgeon. Staples are then placed sequentially along the wound to be closed.

The commonly accepted procedure is to manually approximate the wound margins prior to the staple insertion. If the tissue margins are closely approximated prior to the staples being placed, i.e. in common practice in contact with each other, there will be excessive tissue captured within the staple on closure.

The width of the anvil plate over which the staple is bent determines the final internal staple width. The width between the tines of the staple in its open (unbent) condition is usually about twice the width of the anvil plate over which the staple is bent. As the staple is bent around the anvil plate, the staple closes capturing all tissues caught between the staple tines, which results in about double the optimal quantity of tissue becoming encompassed within the staple on its closure.

Optimal wound margin spacing and alignment requires a very skilled surgeon who is capable of leaving a sufficient yet proper wound gap when placing the staples. Proper initial staple placement will assure accurate alignment of the tissues when the staple is subsequently closed. When too little tissue is enclosed, gaps result. The resultant dead spaces allow easy foreign matter and microbial invasion and also the collection of serum and blood, which provide an ideal medium for the growth of microorganisms that cause infection.

Conversely, when too much tissue is enclosed initially, closure causes tissue compression so that both wound healing and resultant cosmetic appearance are compromised. Several possible mechanical complications and consequences may result from enclosing too much tissue within the confines of the closed staples. With currently commercially available staplers, it is common to see longer wound closures exhibit a combination of such consequences.

The relative sharpness of the points of the staples as well as the relative angle at which the staples are placed greatly effect the end result. If the conventional stapler is held at an angle such that one side is held more tightly against the tissues, one end of the staple will more efficiently penetrate the tissues. The staple will be inserted at an angle and the wound margin first penetrated may be carried upward forcing it to override the opposing wound margin thus exposing raw tissue. The opposite wound margin may be forced underneath when the staple is closed. Tissue margin overlapping which results in the exposure of raw tissue is the most common imperfection seen in surgical closures. In that a surgeon will see the results of partial closure with the resultant overlapping, compensation is made resulting in overlapping of the alternate side. It is common to see wound closures with alternating raw tissue margins exposed.

The crushing apposition of unlike tissues retards healing by requiring the deposition of vast quantities of fibrous connective tissue to bridge the faults thus resulting in significant scarring. Additionally, crushing causes blood supply strangulation which compromises all healing.

Even when the conventional stapler is placed squarely across a wound with approximated tissue margins, the excessive tissue collected between the straight staple ends will be forced tightly together upon closing. This can result in either forcing both tissue margins to be turned outward exposing the raw margins, both being turned inward retarding healing, or the margins properly approximated yet crushed together. These three imperfections are not common because tissue strength and integrity usually forces the wound margin on one side to override the other.

Tensile strength of the tissues to be closed greatly affects healing time. The high tissue strength of skin and fascia provide excellent staple holding characteristics but their relatively limited blood supply limits the healing process. When tissue entrapment occurs within staples, blood supply can be severely compromised which additionally retards healing thus inviting tissue necrosis. At least some degree of necrosis occurs in all cases following staple crushing of tissues and the resultant ischemia. Healing is then compromised until collateral circulation forms and the healing processes established.

When too much tissue is enclosed within the confines of the staples so that tissue compression occurs, additional ischemia produced by the post surgical swelling compromises healing even further. Conversely when the tissue volume within the confines of the closed staple approximates the normal mass of tissue that would ordinarily be present, expected post surgical or post trauma swelling merely assures excellent tissue approximation between sequentially placed staples.

The present invention overcomes the above stated problems, and is distinguished over the prior art by a surgical stapler having a tissue spacer at its forward end. The spacer is inserted between lateral sides of a wound to be closed and holds the tissue on lateral sides of the wound apart while the tines of a staple are driven into the tissue margins and bent around the staple bending surface of the staple anvil to draw the tissue captured between the tines toward each other. The tissue spacer has a width greater than the width of the staple bending surface of the anvil and less than the distance between the tines of the staple in an unbent condition such that when inserted between lateral sides of the wound it will space the facing tissue margins or the wound apart a distance sufficient to provide a metered amount of tissue lateral sides of the wound that will be captured between the tines and drawn together as the tines are bent toward each other to close the wound without crushing or overlapping of the captured tissue.

SUMMARY OF THE INVENTION

It is therefore an object of the present invention to provide a surgical stapler that can be used to properly space and align the tissues to be closed.

It is another object of the present invention to provide a surgical stapler capable of closing wounds sufficiently tight to eliminate dead space yet loose enough to minimize patient discomfort, ischemia and tissue necrosis during healing.

Another object of this invention is to provide a surgical stapler that assures consistent insertion of the staple tines at the optimal distance from the wound margins.

Another object of this invention is to provide a surgical stapler that assures accurate centering of the staple over the incision.

Another object of this invention is to provide a surgical stapler that precludes tissue margin overriding that commonly results when operators use conventional surgical staplers thereby significantly limiting scarring and keloid formation.

Another object of this invention is to provide a surgical stapler that virtually eliminates the possibility of closing wounds with the wound edges being crushed together.

Another object of this invention is to provide a surgical stapler that can be effectively used by surgeons with limited experience as well as skilled artisans.

Another object of this invention is to provide a surgical stapler that assures individual wound margin tissue layer spacing and alignment that launches the most rapid healing.

Another object of this invention is to provide a stapler for wound closure that will limit compromise of blood circulation.

Another object of this invention is to provide a surgical stapler that promotes healing by first intention by close approximation of individual tissue layers.

Another object of this invention is to provide a surgical stapler that allows the use of very fine wire staples thereby minimizing scarring both of the incision and of the staples themselves.

A further object of this invention to provide a surgical stapler that can be used in plastic and cosmetic surgery to achieve cosmetically pleasing results.

A still further object of this invention is to provide a surgical stapler that is simple in construction, inexpensive to manufacture, and rugged and reliable in operation.

These and other objects are accomplished by a surgical stapler having a tissue spacer at its forward end. The spacer is inserted between lateral sides of a wound to be closed and holds the tissue on lateral sides of the wound apart while the tines of a staple are driven into the tissue margins and bent around the staple bending surface of the staple anvil to draw the tissue captured between the tines toward each other. The tissue spacer has a width greater than the width of the staple bending surface of the anvil and less than the distance between the tines of the staple in an unbent condition such that when inserted between lateral sides of the wound it will space the facing tissue margins of the wound apart a distance sufficient to provide a metered amount of tissue lateral sides of the wound that will be captured between the tines and drawn together as the tines are bent toward each other to close the wound without crushing or overlapping of the captured tissue.

BRIEF DESCRIPTION OF THE DRAWINGS

FIG. 1 is a partial perspective view of a preferred embodiment of the surgical stapler having a tissue spacer, shown with the tissue spacer in a wound to establish optimal staple placement prior to closing the wound.

FIG. 2 is a side elevation of the surgical stapler of FIG. 1.

FIGS. 3A and 3B are partial perspective views of the front end of the surgical stapler, shown with the tissue spacer in a raised position and a lowered position, respectively.

FIG. 4 is a partial cross sectional view of an embodiment of the tissue spacer which is raised and lowered vertically by the operation of the trigger of the stapler.

FIG. 5 is a partial cross sectional view of an embodiment of the tissue spacer that is pivoted between a raised and lowered position by the operation of the trigger of the stapler.

FIG. 6 is a side elevation in partial cross section of a tissue stapler having a trigger with a forward end disposed in the stapler body and a pivotal tissue spacer mounted at the front end thereof and operated by the internal trigger mechanism.

FIG. 7 is a partial cross sectional view of a surgical stapler having a rotatable tissue spacer.

FIGS. 8A and 8B are partial perspective views of the front end of the stapler embodiment of FIG. 7, showing the rotatable tissue spacer in a first position rotated for placement in the wound, and a second position rotated to allow wound closure and withdrawal from the wound, respectively.

FIGS. 14A and 14B are cross sectional views of an improved wound closure utilizing the present stapler and tissue spacer, showing the staple as it is initially placed into the tissues, and the staple in its closed configuration, respectively, illustrating the establishment of optimal space between wound margins as the staple is initially placed into the tissues, and the result of utilizing the present invention whereby only the optimal amount of tissue is captured within the confines of the closed staple.

FIGS. 15A and 15B are cross sectional views of a typical wound closure utilizing prior art stapling apparatus and conventional close tissue approximation, showing the staple as it is initially placed into the tissues, and the staple in its closed configuration, respectively, illustrating the crushing together of the enclosed wound margins which commonly causes overriding of one of the tissue margins as a result of utilizing prior art stapling apparatus and conventional close tissue approximation.

DETAILED DESCRIPTION OF PREFERRRED EMBODIMENTS

Figure 9:
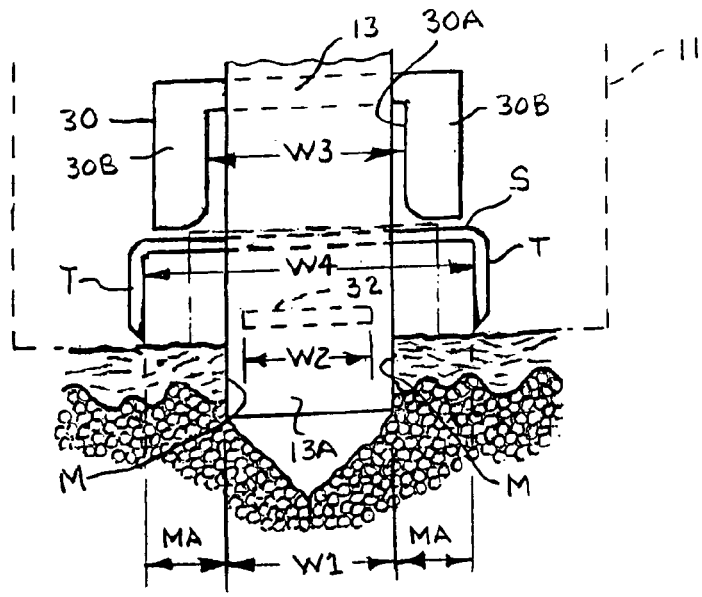
FIGS. 9 and 10 are a front elevation and side elevation, respectively, showing somewhat schematically, the tissue spacer, the staple pusher or driver, and the staple bending surface of the anvil components in a pre-fire position, with the stapler body represented in dashed line and other components which are conventional not shown to avoid confusion.

In the following discussion, it should be understood that many of the internal components and operating mechanisms of the stapler 10 are conventional and well known in the art and therefore not shown in detail. The present stapler may utilize conventional internal components and operating mechanisms such as shown and described in U.S. Pat. Nos. 4,179,057; 4,582,237; 5,038,991; and 5,937,951, which are hereby incorporated by reference, as if set forth herein in their entirety. The present stapler may also utilize either a stationary or movable anvil plate.

Referring now to FIGS. 1, 2, 3A and 3B, there is shown a surgical stapler device 10 in accordance with a preferred embodiment of the present invention, which is used for the closing of wounds, incisions, defects in tissue or the fastening of prosthetics to tissue. The surgical stapler 10 has an elongated body 11 serving as a handle portion. A trigger 12 pivotally mounted to body 11 is operatively connected with a staple driver actuator and an actuator return spring (conventional and therefore not shown). An anvil plate (described in detail hereinafter) supports a row of surgical staples located within a magazine assembly affixed to the lower edges of the body 11. The magazine assembly contains a feeder assembly (conventional and therefore not shown) to constantly urge the row of staples toward a staple bending surface at the forward end of the anvil plate to position the forwardmost staple of the row thereon to be implanted and formed thereabout by the staple driver and to disengage a formed staple therefrom. The release of the stapler trigger 12 actuates the staple driver actuator to advance the next staple into position (conventional and therefore not shown).

A tissue spacer 13 is disposed at the front end 11B of the forward portion 11A of the body 11. In this embodiment, the tissue spacer 13 is a generally rectangular member slidably mounted in a recess 11C formed in the front end 11B of the body 11. The tissue spacer 13 has a finger grip protrusion 14 at its upper end for manually moving the spacer vertically relative to the front end 11B of the stapler body 11 between a raised position (FIG. 3A) and a lower position (FIG. 3B). In its lower position, the bottom end of the tissue spacer 13 depends a short distance beyond the bottom of the front end 11B of the stapler body 11. The bottom portion of the tissue spacer 13 has a width W1. The function of the tissue spacer 13 will be described in detail hereinafter. As seen in FIG. 2, the forward end of the trigger 12 is spring biased to a raised position by a return spring 15.

FIG. 4 shows a second embodiment of a tissue spacer 16 which is raised and lowered vertically by the operation of the trigger 12 of the stapler. In this embodiment, the tissue spacer 16 is a generally rectangular member slidably mounted in a recess formed in the front end 11B of the body 11. The tissue spacer 16 has a recess 16A in its back side which receives a tongue 17A of a cam member 17 rotatably mounted in the body 11. The opposed end of the cam 17 has an arcuate toothed surface 17B similar to a pinion gear which is engaged with a mating toothed rack 18 connected with the forward end of the trigger 12. The forward end of the trigger 12 is spring biased to a raised position by the return spring 15. When the trigger 12 is squeezed, the tissue spacer 16 is moved vertically upward relative to the stapler body by the cam 17, and when the trigger is released, the spacer is returned to its lowered position. The release of the stapler trigger 12 also advances the next staple into position in a conventional manner. In its lower position, the lower end 16B of the tissue spacer 16 depends a short distance beyond the bottom of the front end of the stapler body. The lower portion 16B of the tissue spacer has a width W1 (described hereinafter).

FIG. 5 shows a third embodiment of the tissue spacer 19 which is pivoted between a raised and lowered position by the operation of the trigger 12 of the stapler. In this embodiment, the tissue spacer 19 is a generally rectangular member pivotally mounted in a recess formed in the front end 11B of the body 11. The upper end of the tissue spacer 19 has an arcuate toothed surface 19A similar to a pinion gear which is engaged with a mating toothed rack 18 connected with the forward end of the trigger 12. The forward end of the trigger 12 is spring biased to a raised position by the return spring 15. When the trigger 12 is squeezed, the lower end of the tissue spacer 19 is pivoted upwardly and outwardly relative to the stapler body 11 by the arcuate toothed surface 19A, and when the trigger is released, the spacer pivoted back to its lowered position. The release of the stapler trigger 12 also advances the next staple into position in a conventional manner. In its lower position, the lower end 19B of the tissue spacer 19 depends a short distance beyond the bottom of the front end of the stapler body. The lower end of the tissue spacer 19 has a width W1 (described hereinafter).

FIG. 6 shows the pivoting tissue spacer 19 mounted at the front end of a tissue stapler of the type having a trigger 12A with its forward end disposed within the stapler body 11 wherein the tissue spacer is pivoted by the internal trigger mechanism, in the manner described above.

FIGS. 7, 8A and 8B show a fourth embodiment of a tissue spacer 20 that is rotatable relative to the stapler body 11. In this embodiment, the tissue spacer 20 has an elongate cylindrical shank portion 20A which is rotatably mounted in a recess 11C formed in the front end 11B of the body 11, and a flat generally rectangular lower end 20B which depends a short distance beyond the bottom of the front end of the stapler body. The lower end 20B of the tissue spacer 20 has a width W1. The upper end of the tissue spacer 20 has a spiral groove 21 which receives a pin 22 secured to the forward end of the trigger 12. The forward end of the trigger 12 is spring biased to a raised position by the return spring 15. As shown in FIG. 8A, when the trigger 12 is released or in the relaxed condition and its forward end is raised, the flat rectangular lower end 20B of the tissue spacer 20 is positioned transverse to the longitudinal axis of the stapler body. As shown in FIG. 8B, when the trigger 12 is squeezed, the pin 22 travels downward in the spiral groove 21 to rotate the tissue spacer 20 about its longitudinal axis and the flat rectangular lower end 20B of the tissue spacer is rotated to become aligned parallel and coextensive with longitudinal axis of the stapler body thereby presenting a minimal profile. When the trigger 12 is released, the flat rectangular lower end 20B of the tissue spacer 20 is returned to its transverse position. The release of the stapler trigger also advances the next staple into position in a conventional manner.

Figure 10:
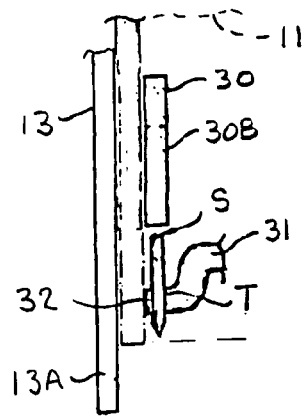

FIGS. 9 and 10 are a front elevation and side elevation, respectively, showing somewhat schematically, the tissue spacer, the staple pusher or driver, and the staple bending surface of the anvil in a pre-fire position, with the stapler body represented in dashed line and other components, which are conventional, are not shown to avoid confusion. The flat rectangular tissue spacer 13 of FIGS. 1–3B is depicted for purposes of illustrating an example, and the components are shown with the stapler in its pre-fire position. It should be understood that each of the embodiments of the tissue spacer described above (13, 16, 19, 20) is mounted at the front end of the stapler body 11 in front of the staple pusher or driver and the staple bending surface of the anvil plate.

In each of the above described stapler embodiments, the forward portion 1A of the body 11 houses a staple pusher or driver 30 attached to a conventional staple driver actuator and return spring for the staple driver actuator (conventional and not shown). The staple pusher or driver 30 is movable between a retracted position and a staple forming position by means of the trigger 12 pivotally mounted to the body 11 and operatively connected with the staple driver actuator. The release of the trigger 12 actuates the staple driver actuator to advance the next staple into position. An anvil plate 31 that supports a row of surgical staples is located within a conventional magazine assembly affixed to the lower edges of the body 11. The anvil plate 31 (hereinafter referred to as anvil) has a staple bending surface 32 at its forward end. The magazine assembly contains a feeder assembly (conventional and not shown) to constantly urge the row of staples toward the staple bending surface 32 to position the forwardmost staple S of the row thereon to be implanted and formed thereabout by the staple driver 30 and to disengage a formed staple therefrom.

The tissue spacer 13 is shown in its lowered position with its lower end 13A placed between the tissue margins M of a wound to be closed. The tissue spacer 13 is disposed in front of the staple pusher or driver 30 and the staple bending surface 32 of the anvil 31, which are shown in position to bend a conventional surgical staple S over the staple bending surface of the anvil when the stapler is activated. The staple bending surface 32 of the anvil 31 has a width W2. The staple pusher or driver 30 has an inverted generally U-shaped recess 30 with lateral sides 30B that engage the staple S, which is preformed in a broad-based, square-cornered U shape, and move downwardly toward the staple bending surface 32 of the anvil 31. The inverted U-shaped recess 30A in the staple pusher or driver 30 has a width W3 which is greater than the width W2 of the staple bending surface 32, but less than the distance or width W4 between the tines T of the staple S, so as to cause the tines to converge inwardly as the staple is bent around the staple bending surface.

Figure 11:
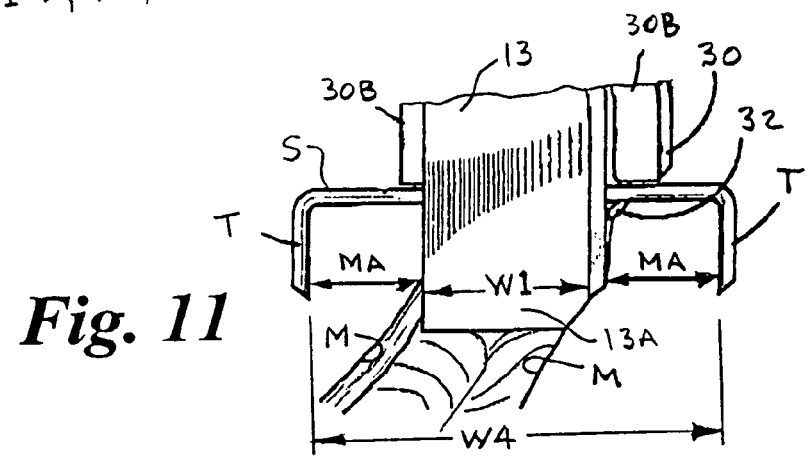
FIG. 11 is a partial perspective view of the tissue spacer in its initial placement in a wound to establish optimal staple placement, prior to insertion of the staple into the tissue.

As represented in FIGS. 9 and 11, in each of the above described embodiments, the width W1 of the lower end of the tissue spacer 13, 16, 19, or the flat rectangular lower end 20B of the rotatable spacer 20, is greater than the width W2 of the staple bending surface 32 of the anvil 31 which lies immediately behind it, and less than the distance or width W4 between the tines T of the staple S in its unbent condition. The width W1 of the tissue spacer is correlated to the staple bending surface W1 of the anvil and the distance or width W4 between the tines T of the staple such that when its lower end is placed in the wound to be closed it will spread the facing tissue margins M at the lateral sides of the spacer apart a distance greater than the width W2 of the anvil bending surface 32 of the anvil 31, but less than the distance or width W4 between the unbent staple tines T and provide a metered transverse linear amount of tissue MA on each side of the wound fore and aft of the spacer. The metered amount of tissue MA will be captured between the tines T of the staple S and drawn into approximation as the tines are bent closed and the spacer is retracted. The amount of tissue captured within the subsequently closed staple will be sufficient to assure wound closure with close and proper approximation of the tissues while preventing crushing and devitalizing the impounded tissue. The lateral edges of the generally rectangular lower end of the tissue spacer are preferably smoothly rounded to allow vertical, linear, or rotary movement with minimal damage to adjacent tissues and with no significant reopening of clotted severed vessels.

OPERATION

Referring now to FIGS. 9, 11, 12 and 13A–13D, the process of wound closure utilizing the present invention will be described using the embodiment of the generally rectangular vertically raised and lowered tissue spacer 13, as an example.

Figure 12:
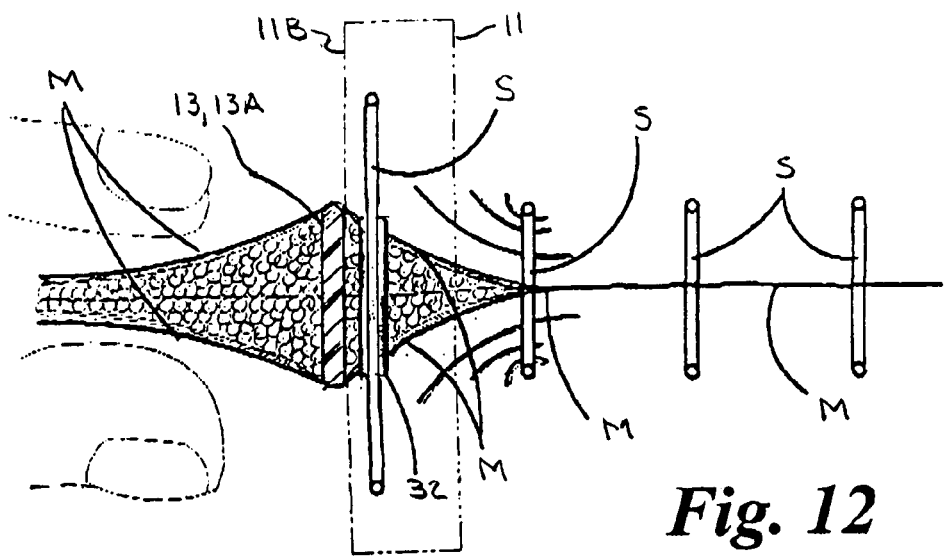
FIG. 12 is a top view illustrating schematically, the process of wound closure showing the manual approximation of the wound margins, the placement of the tissue spacer between the wound margins, the insertion of the staple points into the tissues to be closed and the wound closure that results from closure of the staple.

The wound margins M are manually held in near apposition by manual approximation of the wound margins as if the wound were to be closed in the conventional manner (FIG. 12). The front end 11B of the body 11 of the surgical stapler is pressed against the tissues to be closed with the lower end 13A of the tissue spacer 13 in its lower position inserted into the wound to spread the wound margins slightly apart. The lower end 13A of the tissue spacer 13 separates the tissue margins M so that the total transverse linear amount of tissue (MA+MA) to be captured between the tines T of the staple S slightly exceeds the width W1 of the tissue spacer lower end. As seen in FIGS. 9, 11 and 12, the staple anvil bending surface 32 is in position to hold the center of the staple S facilitating bending both of its extremities by the downward movement of the lateral sides 30B of the recess 30A of the staple pusher or driver 30, or the upward movement of the staple bending surface 32 in staplers of the type having a movable anvil configuration.

Figure 13A:
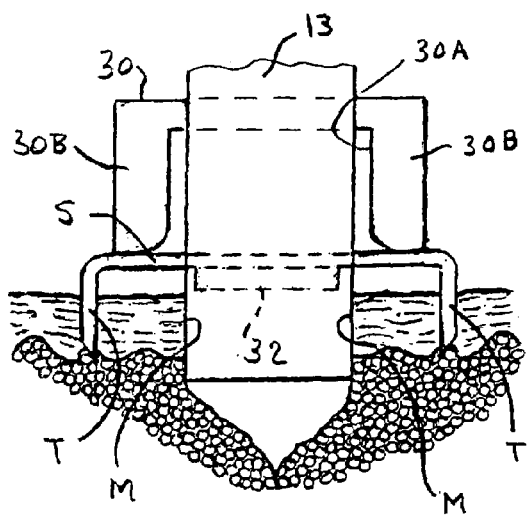
FIGS. 13A, 13B, 13C and 13D are sequential front elevation views illustrating the initial insertion of the staple into the tissues to be closed which are separated by the tissue spacer, the initial bending of the staple with the tissue spacer still in place, the subsequent retraction of the tissue spacer but prior to the further bending of the staple for its complete closure, and the completed bending and closure of the staple with the wound closed with proper alignment of the tissues within the confines of the staple, respectively.
Figure 13B:
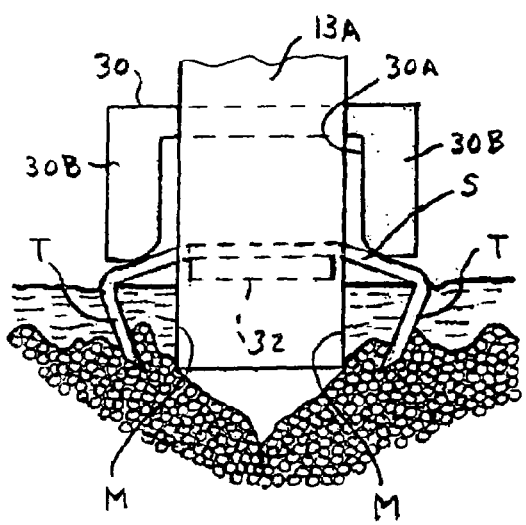
Figure 13C:
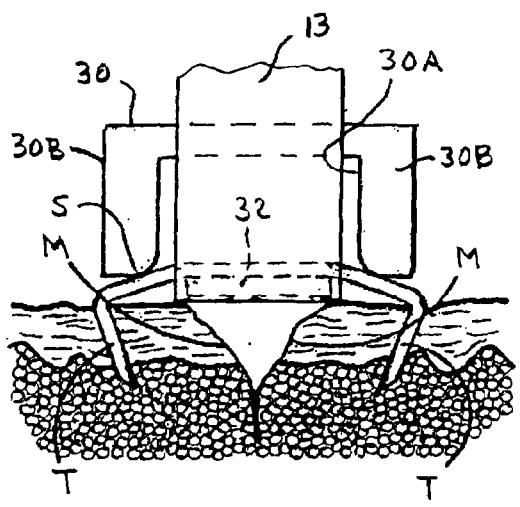
Figure 13D:
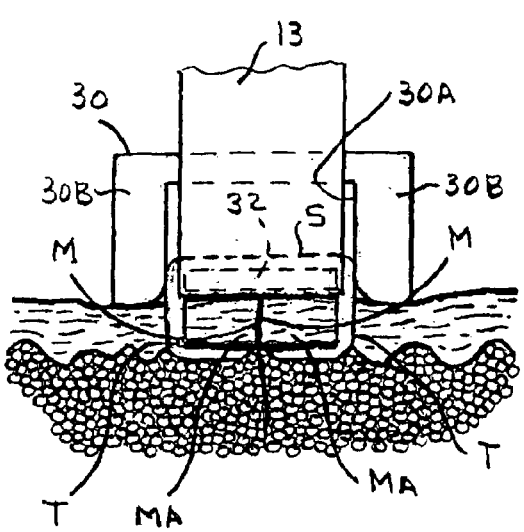

When the tissue margins MA are properly positioned, the trigger is squeezed to advance the staple S and bottom of the sides 30B of the recess of the staple pusher or driver 30 toward the staple bending surface 32 of the anvil (or vice versa). The tissue spacer 13 holds the tissue margins M apart as the staple pusher or driver 30 pushes the staple tines T into the metered tissue MA on the respective opposite sides of the incision or wound (FIG. 13A). On continued squeezing of the trigger the staple S engages the staple bending surface 32 of the anvil and the staple pusher or driver 30 engages the top of the staple and causes the staple to bend around the staple bending surface driving the staple tines T centrally toward each other (FIGS. 13B and 13C) to form a closed, square-cornered C shape capturing only the amount of tissue MA previously metered between the tines T of the staple (FIG. 13D). The tissue spacer 13 continues to hold the wound margins M that are in front of the staple apart while the staple is formed to assure proper tissue penetration by the staple tines T. Thus the tissue spacer 13 acts in the dual capacity of not allowing the tissue margins M to closely approximate thereby establishing the proper alignment of the tissue margins and also serves to support the tissues laterally when the staple is inserted through the metered tissue MA and closed to assure complete and accurate penetration of the staple points into the tissues. The complete closure of the staple S aligns the wound margins M without overlapping or crushing the tissue.

After the staple S has been formed, the pressure on the trigger is released and the tissue spacer 13 is retracted (manually, by releasing the trigger, or upward pivotal movement, or rotation, depending upon the embodiment of the tissue spacer). The stapler is then advanced longitudinally along the wound to the next location and the process is repeated (FIG. 12).

FIGS. 14A and 14B show the improved wound closure utilizing the present stapler and tissue spacer, showing the staple S as it is initially placed into the tissues, and the staple in its closed configuration, respectively, illustrating the establishment of optimal space X between the tissue margins M as the staple is initially placed into the tissues, and the result of utilizing the present invention whereby only the optimal amount of tissue is captured and drawn together within the confines of the closed staple without overlapping or crushing the tissue.

By contrast, FIGS. 15A and 15B show a typical wound closure utilizing prior art stapling apparatus and conventional close tissue approximation methods. The staple tines T are inserted into the tissues at a distance from the wound margins M arbitrarily determined by the closeness of the wound margins relative to the internal width W4 of the staple S (FIG. 15A). FIG. 15B shows the relative position of a final configuration of the staple S as placed using the prior art technique. The staple S has been bent causing the staple to close thus capturing all of the tissue MX that was previously captured between the tines T of the staple during insertion. This causes the crushing together of the enclosed wound tissues MX which commonly causes overriding of one of the tissue margins.

The present invention, on the other hand, allows the closing of wounds with near perfect tissue layer alignment, without crushing excessive captured tissue on closing of the staple, and allows the use of much finer wire staples. Cosmetic surgery incisions can now be closed with staples that assure exceptional tissue alignment while inflicting minimal wound margin damage if very fine wire staples are used. Because the present invention prevents crushing of vast amounts of tissue, fine wire staples, especially somewhat flattened staples may be used to provide the necessary strength required for wound closure without significant tissue damage from the staple puncture wounds.

Significant staple scarring is also avoided when the closing of the staples has not devitalized the enclosed tissues. Especially in wounds with significant swelling, tight staples easily cut through their enclosed trauma induced necrotic tissue, thereby producing staple cutting that may resulting in considerable staple scarring. The present invention precludes this complication and unsightly result by enclosing an optimal amount of tissue within the staple on initial placement.

While this invention has been described fully and completely with special emphasis upon preferred embodiments, it should be understood that within the scope of the appended claims the invention may be practiced otherwise than as specifically described herein.

What is claimed is:

1. A surgical stapler for closing wounds in tissue, comprising:

a housing with a forward end;

a chamber for receiving surgical staples having laterally spaced tines;

an anvil with a staple bending surface having a width for receiving a staple in an unbent condition;

a staple driver for driving the laterally spaced tines of the staple into margins of tissue on lateral sides of the wound and bending the staple around the staple bending surface to draw the tines and the margins of the tissue captured therebetween toward each other;

an actuator trigger connected with either of said staple driver or said anvil for moving one relative to the other between a retracted position and a staple forming position; and a tissue spacer at a forward end of said housing having a lower end adapted to be removably positioned between lateral sides of the wound to space and hold facing margins of tissue on lateral sides of the wound apart while the staple tines are inserted into the margins of tissue and the staple is bent around said staple bending surface to close the staple tines and draw the tissue margins captured therebetween toward each other; and said lower end having a width greater than the width of said stable bending surface and less than the distance between the tines of the staple in an unbent condition to provide a metered amount of tissue on lateral sides of the wound to be captured between the staple tines such that the facing margins of tissue are drawn together to close the wound without crushing or overlapping of the captured tissue.

2. The surgical stapler according to claim 1, wherein said tissue spacer is movably connected with said surgical stapler for movement relative to said housing between a first position to engage lateral sides of the wound, and a second position disengaged from the lateral sides of the wound.

3. The surgical stapler according to claim 2, wherein said tissue spacer is disposed at a forward end of said housing and is movable relative to said housing between a lower position to engage lateral sides of the wound, and a raised position disengaged from the lateral sides of the wound.

4. The surgical stapler according to claim 3, wherein said tissue spacer is slidably mounted at a forward end of said housing and is manually movable relative to the stapler housing between said lower position and said raised position.

5. The surgical stapler according to claim 3, wherein said tissue spacer is operatively connected with said actuator trigger to move relative to said housing to said raised position when said trigger is squeezed and return to said lower position when said trigger is released.

6. The surgical stapler according to claim 3, wherein said tissue spacer is pivotally mounted at a forward end of said housing and is pivoted about a horizontal axis relative to said housing between said lower position and said raised position.

7. The surgical stapler according to claim 6, wherein said tissue spacer is operatively connected with said actuator trigger to be pivoted thereby to said raised position when said trigger is squeezed and return to said lower position when said trigger is released.

8. The surgical stapler according to claim 2, wherein said tissue spacer is disposed at a forward end of said housing and has a generally rectangular lower end rotatable about a vertical axis relative to said housing between said first position to engage lateral sides of the wound, and said second position disengaged from the lateral sides of the wound.

9. The surgical stapler according to claim 8, wherein said tissue spacer is operatively connected with said actuator trigger to move said generally rectangular lower end to said second position when said trigger is squeezed and return to said first position when said trigger is released.

10. An improved surgical stapler for closing wounds in tissue and having a housing with a forward end, a chamber for receiving surgical staples having laterally spaced tines, an anvil with a staple bending surface having a width for receiving a staple in an unbent condition, a staple driver for driving laterally spaced tines of a staple into margins of tissue on lateral sides of the wound and bending the staple around the staple bending surface to draw the tines and the margins of the tissue captured therebetween toward each other, and an actuator trigger connected with either of said staple driver or said anvil for moving one relative to the other between a retracted position and a staple forming position, the improved surgical stapler further comprising:

a tissue spacer device at the forward end of the surgical stapler having a lower end adapted to be removably inserted between lateral sides of the wound to space and hold facing margins of tissue on lateral sides of the wound apart while the staple tines are inserted into the margins of tissue and the staple is bent around the staple bending surface to close the staple tines and draw the tissue margins captured therebetween toward each other; and said lower end having a width greater than the width of said stable bending surface and less than the distance between the tines of the staple in an unbent condition to provide a metered amount of tissue on lateral sides of the wound to be captured between the staple tines such that the facing margins of tissue are drawn together to close the wound without crushing or overlapping of the captured tissue.

11. The improved surgical stapler according to claim 10, wherein said tissue spacer device is movably connected with the surgical stapler for movement relative to the stapler housing between a first position to engage lateral sides of the wound, and a second position disengaged from the lateral sides of the wound.

12. The improved surgical stapler according to claim 11, wherein said tissue spacer device is disposed at a forward end the stapler housing and is movable relative to the stapler housing between a lower position to engage lateral sides of the wound, and a raised position disengaged from the lateral sides of the wound.

13. The improved surgical stapler according to claim 12, wherein said tissue spacer device is slidably mounted at the forward end of the stapler housing and is manually movable relative to the stapler housing between said lower position and said raised position.

14. The improved surgical stapler it according to claim 12, wherein said tissue spacer device is operatively connected with the actuator trigger to move relative to the stapler housing to said raised position when said trigger is squeezed and return to said lower position when said trigger is released.

15. The improved surgical stapler according to claim 12, wherein
said tissue spacer device is pivotally mounted at the forward end of the stapler housing and is pivoted about a horizontal axis relative to the stapler housing between said lower position and said raised position.

16. The improved surgical stapler it according to claim 15, wherein
said tissue spacer device is operatively connected with the actuator trigger to be pivoted thereby to raised position when said trigger is squeezed and return to said lower position when said trigger is released.

17. The improved surgical stapler according to claim 11, wherein
said tissue spacer device is disposed at the forward end of the stapler housing and has a generally rectangular lower end rotatable about a vertical axis relative to the stapler housing between said first position to engage lateral sides of the wound, and said second position disengaged from the lateral sides of the wound.

18. The improved surgical stapler it according to claim 17, wherein
said tissue spacer device is operatively connected with the actuator trigger to move said generally rectangular lower end to said second position when said trigger is squeezed and return to said first position when said trigger is released.

19. A surgical stapling method for closing wounds in tissue, comprising the steps of:
providing a surgical stapler having a stable bending surface and a tissue spacer at the forward end of thereof, the tissue spacer having a lower end of a width greater than the width of the stable bending surface and less than the distance between the tines of a staple in an unbent condition;

manually holding the tissue margins on lateral sides of a wound to be closed in near apposition;

positioning the spacer into the wound to space and hold the facing tissue margins apart a distance sufficient to provide a transverse metered amount of tissue on laterally opposed sides of the wound that is to be captured between the tines of the staple to be driven into the tissue margins;

pressing the surgical stapler against the tissues to be closed;

operating the stapler to drive the tines of the staple into the tissue margins on respective laterally opposed sides of the wound and bend the staple to drive the ends of the tines centrally toward each other to form a closed generally square-cornered C shape capturing the metered amount of tissue between the tines of the staple; and thereafter retracting the spacer from the wound; whereby the wound margins that are adjacent to the staple are held apart and supported laterally by the spacer to facilitate proper tissue penetration by the staple tines during insertion and closure of the staple, and the metered amount of tissue on lateral sides of the wound that is captured between the staple tines is drawn together to close the wound without crushing or overlapping of the captured tissue.

\* \* \* \* \*